US007393672B2

(12) United States Patent
Muramatsu et al.

(10) Patent No.: US 7,393,672 B2
(45) Date of Patent: Jul. 1, 2008

(54) DNA CODING FOR ENDO-β-GALACTOSIDASE

(75) Inventors: Takashi Muramatsu, Nagoya (JP); Haruko Ogawa, Arlington Heights, IL (US); Hisako Muramatsu, Nagoya (JP); Takaaki Kobayashi, Nagoya (JP); Itsuo Yokoyama, Nagoya (JP)

(73) Assignee: Seikagaku Corporation, Chuo-ku, Tokyo (JP)

( * ) Notice: Subject to any disclaimer, the term of this patent is extended or adjusted under 35 U.S.C. 154(b) by 0 days.

(21) Appl. No.: 11/407,596

(22) Filed: Apr. 20, 2006

(65) Prior Publication Data

US 2006/0177427 A1 Aug. 10, 2006

Related U.S. Application Data

(62) Division of application No. 10/111,349, filed as application No. PCT/JP00/07347 on Oct. 20, 2000, now Pat. No. 7,060,483.

(30) Foreign Application Priority Data

Oct. 22, 1999 (JP) ................................ 11-300795

(51) Int. Cl.
*C12N 9/38* (2006.01)

(52) U.S. Cl. ...................................... 435/207; 536/23.2

(58) Field of Classification Search ................. 435/207, 435/252.3, 320.1; 536/23.2
See application file for complete search history.

(56) References Cited

U.S. PATENT DOCUMENTS 5,925,541 A 7/1999 Goldstein ................... 435/207

FOREIGN PATENT DOCUMENTS

| | | |
|---|---|---|
| JP | 63-042877 | 3/1988 |
| JP | 63-052877 | 3/1988 |
| JP | 10-201472 | 8/1998 |
| WO | WO 91/04335 | 4/1991 |
| WO | WO 98/11246 | 3/1998 |

OTHER PUBLICATIONS

Sequence search alignment between Acc. No. Q59328 and SEQ ID No. 2.*
Ogawa, et al. *Cell Technology, Special Issue: New Stage of Organ Transplantation; From Xenotransplantation to Cell Transplantation*, vol. 19, No. 6, Jun. 2000, pp. 344, 846-848. English translation of title, abstract, selected sections and figure legend.
Ogawa, et al. "Endo-beta-galactosidase C precursor," Database accession No. Q9KWF3, XP002238200, Oct. 1, 2000.
Supplementary European Search Report issued in a related foreign application dated Apr. 14, 2003.
Ogawa, H., et al. "Molecular Cloning of Endo-β-galactosidase C and Its Application in Removing α-Galactosyl Xenoantigen from Blood Vessels in the Pig Kidney," *The Journal of Biological Chemistry*, vol. 275, No. 25, Jun. 2000. pp. 19368-19374.
The 5th Congress of the International Xenotransplantation Association. "Transplantation Proceedings," Oct. 24-28, 1999, Nagoya, Japan.

* cited by examiner

*Primary Examiner*—Tekchand Saidha
(74) *Attorney, Agent, or Firm*—Knobbe, Martens, Olson & Bear, LLP

(57) ABSTRACT

A full-length cDNA is obtained by analyzing the partial amino acid sequence of purified endo-β-galactosidase C, constructing primers based thereon, effecting PCR with the use of the genomic DNA of *Clostridium perfringens* as a template to thereby obtain a fragment of cDNA encoding endo-β-galactosidase, effecting cassette PCR by using the cDNA fragment thus obtained to thereby obtain the 5'-terminal and 3'-terminal domains, and further effecting PCR with the use of primers constructed on the basis of the data acquired above.

5 Claims, 4 Drawing Sheets

DNA CODING FOR ENDO-β-GALACTOSIDASE

This is a divisional of U.S. application Ser. No. 10/111,349, filed Apr. 22, 2002, Now U.S. Pat. No. 7,060,483 which is the U.S. National Phase under 35 U.S.C. § 371 of International Application PCT/JP00/07347, filed Oct. 20, 2000, which claims priority of Japanese Patent Application No. 11-300795, filed Oct. 22, 1999.

FIELD OF THE INVENTION

The present invention relates to a DNA coding for an endo-β-galactosidase, a recombinant vector incorporated with the DNA, a transformant transformed with the DNA or the recombinant vector and a method for producing the endo-β-galactosidase by using the transformant.

The present invention further relates to an agent for treating an organ, which contains the endo-β-galactosidase and an organ obtained by treating an organ with the agent for treatment.

BACKGROUND ART

Endo-β-galactosidase derived from *Clostridium perfringens* (hereinafter referred to as "endo-β-galactosidase C") is an enzyme that acts on the Galα1->3Galβ1->4GlcNAc sequence at a terminus of a glycoconjugate and digests the Galβ1->4GlcNAc linkage, but does not act on the Galα1->3 (Fucα1->2)Galβ1->4GlcNAc sequence (Japanese Patent Publication (Kokoku) No. 7-87783). This enzyme is useful as an analytical reagent.

This enzyme can be prepared by culturing *Clostridium perfringens*. If a DNA coding for this enzyme is obtained, production of the enzyme in a further larger amount by a genetic engineering technique will become possible. There is also possibility of utilizing this enzyme for xenotransplantation as described later.

DISCLOSURE OF THE INVENTION

Accordingly, an object of the present invention is to provide a large amount of the endo-β-galactosidase C in a pure form at low cost by a genetic engineering technique by isolating a DNA coding for the endo-β-galactosidase C.

Further, another object of the present invention is to provide an agent for treating organ containing the endo-β-galactosidase C, which is particularly useful for xenotransplantation, and further provide an organ useful for xenotransplantation.

The inventors of the present invention assiduously studied in order to achieve the aforementioned objects. As a result, they isolated a DNA coding for the endo-β-galactosidase C and elucidated its nucleotide sequence, and moreover, they confirmed that this DNA expressed the endo-β-galactosidase C having enzymatic activity. Thus, they accomplished the present invention.

That is, the present invention provides a DNA coding for a protein defined in the following (A) or (B) (hereinafter, also referred to as the "DNA of the present invention"):

(A) a protein that comprises the amino acid sequence of SEQ ID NO: 2;

(B) a protein that comprises an amino acid sequence having an amino acid sequence of (A) including substitution, deletion, insertion or transposition of one or several amino acids and has endo-β-galactosidase activity.

The present invention provides the aforementioned DNA, wherein the protein having an amino acid sequence of (A) includes substitution, deletion, insertion or transposition of one or several amino acids and having endo-β-galactosidase activity is a protein having the amino acid sequence represented by the amino acid numbers 35 to 845 in SEQ ID NO: 2.

Preferred examples of such a DNA include a DNA defined in the following (a) or (b):

(a) a DNA that comprises the nucleotide sequence of the nucleotide numbers 246 to 2780 in SEQ ID NO: 1;

(b) a DNA that is hybridizable with a DNA having all or a part of a nucleotide sequence complementary to the nucleotide sequence of the nucleotide numbers 246 to 2780 in SEQ ID NO: 1 under the stringent conditions, and codes for a protein having endo-β-galactosidase activity.

Preferred examples of the aforementioned DNA further include a DNA defined in the following (a) or (b):

(a) a DNA that comprises the nucleotide sequence of the nucleotide numbers 348 to 2780 in SEQ ID NO: 1;

(b) a DNA that is hybridizable with a DNA having all or a part of a nucleotide sequence complementary to the nucleotide sequence of the nucleotide numbers 348 to 2780 in SEQ ID NO: 1 under the stringent conditions, and codes for a protein having endo-β-galactosidase activity.

The present invention also provides a recombinant vector incorporated with the DNA of the present invention (hereinafter, also referred to as the "recombinant vector of the present invention"). Further, the present invention provides a transformant obtained by introducing the DNA of the present invention or the recombinant vector of the present invention into a cell is (hereinafter, also referred to as the "transformant of the present invention").

The present invention also provides a method for producing endo-β-galactosidase, which comprises growing the transformant of the present invention to allow expression of a DNA coding for the endo-β-galactosidase and collecting the produced endo-β-galactosidase (hereinafter, also referred to as the "production method of the present invention").

The present invention also provides an agent for treating an organ, which contains the endo-β-galactosidase (hereinafter, also referred to as the "agent for treatment of the present invention"). The agent for treatment of the present invention is preferably an agent for treating an organ for transplantation, and the organ to be treated is preferably an organ expressing α-galactose antigens. As such an organ for transplantation, a swine organ is preferred, and an organ for transplantation to a human is further preferred. For example, kidney can be mentioned as a preferred example.

The present invention also provides an organ obtained by treating an organ expressing α-galactose antigens with the agent for treatment of the present invention (hereinafter, also referred to as the "organ of the present invention").

The present invention also provides a method for producing an organ for transplantation showing suppressed rejection due to α-galactose antigens, which comprises treating an organ expressing α-galactose antigens with the endo-β-galactosidase.

In the present invention, endo-β-galactosidase activity refers to an activity for catalyzing a reaction of cleaving a Galβ1->4GlcNAc linkage of Galα1->3Galβ1->4GlcNAc sequence at a terminus of glycoconjugate.

Hereafter, the present invention will be described in detail.

<1> DNA of the Present Invention

The DNA of the present invention is a DNA coding for a protein defined in the following (A) or (B):

(A) a protein that comprises the amino acid sequence of SEQ ID NO: 2;

(B) a protein that comprises an amino acid sequence having an amino acid sequence of (A) including substitution, deletion, insertion or transposition of one or several amino acids and has endo-β-galactosidase activity.

Especially, a DNA coding for the protein defined in (A) is preferred.

In the present specification, the expression "a protein that comprises an amino acid sequence including substitution, deletion, insertion or transposition of one or several amino acids and has endo-β-galactosidase activity" means that the protein may include substitution, deletion, insertion or transposition of one or several amino acid residues that does not substantially impair activity for acting on the Galα1->3Galβ1->4GlcNAc sequence at a terminus of a glycoconjugate to cleave the Galβ1->4GlcNAc linkage (endo-β-galactosidase activity).

That is, it is known that, in a naturally occurring protein, a mutation such as substitution, deletion, insertion or transposition of an amino acid can occur in the amino acid sequence due to polymorphism or mutation of DNA coding for it as well as a modification reaction of a produced protein in an living body or during purification, but, in spite of such a mutation, there may be such a protein still having physiological and biological activities substantially equivalent to those of a protein having no mutation. The DNA of the present invention also includes a DNA coding for a protein that has some structural differences, but does not show significant functional difference.

Similarly, the DNA of the present invention also includes a DNA obtained by artificially introducing such a mutation as described above into a DNA coding for a protein, and more various and diverse mutants can be prepared in such a case. For example, it is known that a protein obtained by replacing a certain cysteine residue with a serine residue in an amino acid sequence in human interleukin 2 (IL-2) has IL-2 activity (Science, 224, 1431 (1984)). Further, some kinds of proteins are known to have a peptide region that is not necessary for activity. Examples of such proteins include a signal peptide present in a protein secreted outside a cell, a pro-sequence observed in a precursor of protease or the like. Most of such regions are eliminated after translation or at the time of conversion into an active protein. Such proteins exist in a different form as for the primary structure, but the proteins ultimately have an equivalent function. A DNA coding for any of such proteins is also included in the DNA of the present invention. For example, a protein having the amino acid sequence of the amino acid numbers 35 to 845 in SEQ ID NO: 2 is a protein that lacks a region corresponding to the amino acid numbers 1 to 34 (considered to correspond to a signal sequence), but has endo-β-galactosidase activity. Therefore, a DNA coding for such a protein is also included in the DNA of the present invention.

The expression "several amino acids" used in the present specification refers to about 2 to 40, preferably 2 to 20, more preferably 2 to 10, of amino acids, when a protein consists of, for example, 800 amino acid residues.

The endo-β-galactosidase activity can be determined by, for example, a determination method utilizing a swine erythrocyte or vascular endothelial cell (the Galα1->3Galβ1->4GlcNAc sequence is present on its surface) and lectin that specifically recognizes the Galα1->3Gal structure as shown in the examples described later. Further, as shown in the examples described later, the endo-β-galactosidase activity can also be determined by allowing an enzymatic reaction using Galα1-3Galβ1-4GlcNAcβ1-3Galβ1-4Glc or the like as a substrate, and analyzing the enzymatic reaction product by thin layer chromatography (TLC), mass spectrometry or the like. Therefore, those skilled in the art can readily select substitution, deletion, insertion or transposition of one or several amino acids that does not substantially impair the endo-β-galactosidase activity by using presence or absence of the activity as an indicator.

The substitution, deletion, insertion or transposition of one or several amino acid residues that does not substantially impair the endo-β-galactosidase activity can occur under a natural condition, or can be obtained by artificially introducing substitution, deletion, insertion or transposition of a nucleotide or nucleotides that would induce such substitution, deletion, insertion or transposition into a DNA coding for the amino acid sequence. The substitution, deletion, insertion or transposition of a nucleotide or nucleotides can be introduced into a DNA by synthesizing a sequence that has restriction enzyme-digested termini at both ends and includes both sides of a mutation point, and replacing a region corresponding to a nucleotide sequence of unmutated DNA with it. Further, substitution, deletion, insertion or transposition of a nucleotide or nucleotides can also be introduced by the site specific mutagenesis (Kramer, W. and Frits, H. J., Meth. in Enzymol., 154, 350 (1987); Kunkel, T. A. et al., Meth. in Enzymol., 154, 367 (1987)) or the like.

As the DNA of the present invention, a DNA including the nucleotide sequence represented by the nucleotide numbers 246 to 2780 in SEQ ID NO: 1 can be specifically exemplified and is preferred. Further, the DNA of the present invention may be a DNA that is hybridizable with a DNA having all or a part of a nucleotide sequence complementary to the nucleotide sequence of the nucleotide numbers 246 to 2780 in SEQ ID NO: 1 under the stringent conditions so long as the encoded protein has the endo-β-galactosidase activity. The "stringent conditions" referred to herein are conditions under which a so-called specific hybrid is formed, but a non-specific hybrid is not formed (refer to Sambrook, J. et al., Molecular Cloning A Laboratory Manual, Second Edition, Cold Spring Harbor Laboratory Press (1989) etc.). The "stringent conditions" include a condition used in usual gene hybridization, for example, a condition used in Southern blotting, Northern blotting or screening using hybridization or the like. Specifically, the stringent conditions are exemplified by a condition for hybridization at 42° C. in the presence of 50% formamide, 5×SSPE (20×SSPC: 3.6 M sodium chloride, 0.2 M sodium phosphate buffer (pH 7.7), 20 mM EDTA disodium), 5× Denhardt's solution and 0.1% SDS.

It will be easily understood by those skilled in the art that a DNA having a different nucleotide sequence due to degeneracy of genetic code is included in the DNA of the present invention so long as the DNA codes for substantially the same amino acid sequence as the amino acid sequence of SEQ ID NO: 2.

The present invention also includes a DNA or RNA complementary to the DNA of the present invention. Further, the DNA of the present invention may be a single-stranded one comprising only a coding strand coding for the endo-β-galactosidase C or a double-stranded one comprising such a single-stranded DNA and a DNA strand or RNA strand having a nucleotide sequence complementary to it.

The DNA of the present invention having the nucleotide sequence shown in the SEQ ID NO: 1 is originally derived from *Clostridium perfringens*. However, its origin is not limited, and a DNA prepared by a genetic engineering technique, chemical synthesis or the like is included as a matter of course. Further, even a DNA obtained by ligating the DNA of the present invention to a DNA having a certain function or coding for another protein or the like is also included in the DNA of the present invention so long as it contains the DNA of the present invention. In the nucleotide sequence of SEQ ID NO: 1, "t" of the nucleotide number 660 may be "c", and the 139th amino acid residue, "Ser", may be "Pro" in the amino acid sequence shown in SEQ ID NOS: 1 and 2. In either case, such a DNA is included in the DNA of the present invention so long as the encoded protein has the endo-β-galactosidase activity.

The DNA of the present invention was obtained by the following genetic engineering technique for the first time.
(1) A partial amino acid sequence of purified endo-β-galactosidase C (Japanese Patent Publication No. 7-87783) is analyzed, and PCR primers are prepared based on the sequence.
(2) PCR is performed by using the primers obtained in (1) and genomic DNA of *Clostridium perfringens* as a template to obtain a partial fragment of cDNA coding for endo-β-galactosidase C.
(3) Cassette PCR is performed by using the partial cDNA obtained in (2) to further obtain regions on the 5' and 3' end sides.
(4) Primers for obtaining a full length cDNA are prepared based on the information obtained in (3) and a full length cDNA is obtained by PCR and analyzed for its nucleotide sequence.

The origin for collecting the DNA of the present invention is not particularly limited so long as it codes for the endo-β-galactosidase C. Specifically, *Clostridium perfringens* ATCC 10873 can be mentioned. This bacterial strain is available from the American Type Culture Collection (12301, Parklawn Drive, Rockville, Md. 20852 U.S.A). Further, this bacterial strain was deposited by the applicant of the present application at the National Institute of Bioscience and Human-Technology, the Agency of Industrial Science and Technology, the Ministry of International Trade and Industry, and received an accession number of FERM P-8917.

<2> Recombinant Vector of the Present Invention and Transformant of the Present Invention The recombinant vector of the present invention is obtained by incorporating the DNA of the present invention into a vector. The recombinant vector of the present invention can be introduced into an appropriate cell or the like, and thereby various functions of the DNA of the present invention can be exhibited.

The vector to be incorporated with the DNA of the present invention is not particularly limited so long as the DNA of the present invention can be incorporated, but an expression vector is preferred.

Further, the DNA of the present invention may be expressed directly or as a fusion polypeptide with another polypeptide. When the DNA of the present invention is expressed as a fusion polypeptide with another polypeptide, the DNA of the present invention is preferably incorporated into an expression vector incorporated with a DNA coding for another polypeptide beforehand.

The DNA of the present invention may be expressed in its full length, or a part thereof may be expressed as a partial peptide. The DNA of the present invention can be appropriately processed and incorporated into an expression vector depending on the desired expression form.

The transformant of the present invention can be obtained by introducing the DNA of the present invention or the recombinant vector of the present invention into a cell. The cell that can be introduced with the DNA of the present invention or the recombinant vector of the present invention is not particularly limited so long as the functions of the DNA of the present invention or the recombinant vector of the present invention can be exhibited, and can be appropriately selected depending on the kind of the vector, purpose and so forth. For example, a prokaryotic cell such as *Escherichia coli* and a eukaryotic cell such as a mammalian cell can be exemplified.

The recombinant vector of the present invention obtained by incorporating the DNA of the present invention into an expression vector can be introduced into a host cell suitable for gene expression, for example, a mammalian cell such as COS-7 cell, *Escherichia coli* (*E. coli* BL-12 cell etc.), insect cell and plant cell and these cells are preferred.

As a method for introducing the DNA of the present invention or the recombinant vector of the present invention into a host cell, a known method can be used. Commercially available reagents used exclusively for this purpose (for example, LIPOFECTAMINE PLUS Reagent (Gibco BRL) etc.) can also be used.

<3> Production Method of the Present Invention

The production method of the present invention is a method for producing the endo-β-galactosidase, which comprises growing the transformant of the present invention to allow expression of a DNA coding for the endo-β-galactosidase and collecting the produced endo-β-galactosidase.

As a specific method for growing the transformant, culture is most preferred, but the transformant can also be grown in an animal or plant body, or as an animal or plant body itself.

For example, the endo-β-galactosidase can be prepared by culturing the transformant of the present invention in a suitable medium to produce and accumulate the endo-β-galactosidase encoded by the DNA of the present invention in culture and collecting the enzyme from the culture.

Some hosts used in the present invention are expected to accumulate the endo-β-galactosidase in their cells. In this case, the endo-β-galactosidase is collected from the cells. Further, depending on the host or form of expression, the endo-β-galactosidase is accumulated in a medium. In this case, the endo-β-galactosidase is collected from the medium.

The growth condition of the transformant of the present invention can be appropriately selected depending on a condition under which a host cell introduced with the DNA of the present invention or the recombinant vector of the present invention can grow (medium, culture conditions etc.), a form of polypeptide to be expressed and so forth. For example, when a COS-7 cell is used as a host cell, it can be cultured at 37° C. in DMEM medium containing about 2% fetal calf serum (FCS). Further, when *Escherichia coli* is used as a host cell, for example, a medium appropriately prepared by using LB medium or the like as a main ingredient can be used.

Further, when the endo-β-galactosidase is to be expressed as a fusion polypeptide with protein A and purified by utilizing specific affinity to IgG, it is preferable to eliminate IgG beforehand from FCS to be added to the medium. IgG can be eliminated by bringing FCS into contact with an IgG-specific ligand, for example, a carrier having protein A, performing solid-liquid separation and collecting the liquid phase.

The endo-β-galactosidase can be collected by an appropriate combination of known methods for extracting and purifying an enzyme. Examples of the methods for extracting an enzyme include treatment operations consisting of, for example, extraction after cell disruption by, for example, homogenization, glass beads mill method, sonication, osmotic shock and freeze-thaw method, surfactant extraction and combinations thereof.

Examples of the methods for purifying the endo-β-galactosidase include treatment operations consisting of, for example, salting out with ammonium sulfate, sodium sulfate or the like, centrifugation, dialysis, ultrafiltration, ion exchange chromatography, gel filtration, affinity chromatography, electrophoresis, combinations thereof and so forth.

Production of the endo-β-galactosidase C can be confirmed by analyzing the amino acid sequence, action, substrate specificity and so forth of the purified enzyme and comparing these with properties of the endo-β-galactosidase C.

The extraction and purification process may be simplified by expressing the endo-β-galactosidase as a fusion polypeptide with another polypeptide. For example, when the DNA of the present invention is expressed as a fusion polypeptide with protein A, the fusion polypeptide is secreted into a culture supernatant, and hence the extraction operation becomes unnecessary. Further, purification can be attained by one step by using a carrier having a ligand specific to protein A (for example, IgG).

In the examples described later, it was confirmed that the endo-β-galactosidase C having enzymatic activity could be expressed by growing the transformant of the present invention under an appropriate condition. Therefore, the production method of the present invention can be used for mass production of the endo-β-galactosidase C having enzymatic activity.

<4> Agent for Treatment of the Present Invention and Organ of the Present Invention The agent for treatment of the present invention is an agent for treating an organ, which contains the endo-β-galactosidase. Further, the organ of the present invention is an organ obtained by treating an organ expressing α-galactose antigens with the agent for treatment of the present invention.

The DNA of the present invention and endo-β-galactosidase to be prepared with it can be used for xenotransplantation. That is, a sugar chain having a Galα1-3Gal structure (α-galactose antigen) exists in swine tissues or the like, but does not exist in human tissues. Therefore, when a swine tissue is transplanted to a human, rejection occurs. Accordingly, if the Galα1-3Gal structure is eliminated from a swine tissue by treating the swine tissue with the endo-β-galactosidase prepared by using the DNA of the present invention, or a swine (clone swine or the like) that does not express the Galα1-3Gal structure is produced by introducing the DNA of the present invention into a swine cell (ES cell or the like), they can be used for xenotransplantation.

Hereafter, the agent for treatment of the present invention and the organ of the present invention will be described in detail.

The main antigen responsible for hyperacute rejection in xenotransplantation is the α-galactose antigen present on cell surfaces. The α-galactose antigen is an antigen having the Galα1-3Gal structure. In old world monkeys including humans, the Galα1-3Gal structure is not present at sugar chain termini of glycoproteins or glycolipids. Therefore, strong natural antibodies directed to this structure are produced. Since most mammals, including swine, have the Galα1-3Gal structure, the natural antibodies bind to the antigens on vascular endothelial cells, thus complement-dependent hyperacute rejection is induced and a blood vessel is destroyed, when, for example, a swine organ is transplanted to a human.

The agent for treatment of the present invention prevents hyperacute rejection by eliminating the α-galactose antigens by the action of endo-β-galactosidase to such an extent that acute rejection due to the antigens should be eliminated.

The endo-β-galactosidase contained in the agent for treatment of the present invention is not particularly limited so long as the enzyme can eliminate the α-galactose antigens (Galα1-3Gal structure), but an enzyme that can eliminate the α-galactose antigen from the Galα1-3Galβ1-4GlcNAc structure is preferred. Among such enzymes, endo-β-galactosidase C is preferred in view of its efficiency of enzymatic action, optimum pH close to neutral, effective actions even at low temperature and so forth. In particular, an endo-β-galactosidase C prepared by the DNA of the present invention can be preferably used.

The agent for treatment of the present invention is preferably used for treatment of an organ for transplantation and treatment of an organ expressing α-galactose antigens. Further, an organ treated with the agent for treatment of the present invention is preferably transplanted to a mammal that does not have the α-galactose antigens on its cell surfaces.

In particular, the organ for transplantation treated with the agent for treatment of the present invention is preferably a swine organ, of which use for xenotransplantation to a human is expected, particularly preferably an organ to be transplanted to a human. Further, as such an organ, kidney, liver, heart, lung and so forth can be exemplified, but kidney is preferred.

The form of the agent for treatment of the present invention as a pharmaceutical can, be appropriately selected depending on the mode of using the agent for treatment of the present invention. For example, the agent can be prepared as a liquid agent, perfusion agent, solid agent dissolved at the time of use and so forth.

For example, when the agent for treatment of the present invention is provided as a liquid agent, the agent may be either in a solution or in a frozen state. This can be filled and sealed in an appropriate container such as a bottle or chemical bag and distributed or stored until use as it is.

When the agent is provided as a solid agent, the form is not limited so long as the endo-β-galactosidase is stable, but, for example, lyophilized agent, spray-dried agent or the like can be exemplified.

Known methods can be used for preparation of the agent for treatment of the present invention as a pharmaceutical. At the time of the preparation as a pharmaceutical, ingredients usually used for drugs such as other pharmaceutically active ingredients, conventionally used excipients, stabilizers, binders, lubricants, emulsifiers, osmotic regulators, pH regulators, buffers, isotonic agents, preservatives, coloring agents and disintegrators can be used, so long as they should not adversely affect the endo-β-galactosidase and an effect obtained by treatment with the endo-β-galactosidase should not be affected.

The agent for treatment of the present invention can be used for the purpose of suppression of hyperacute rejection upon transplantation of an organ. That is, the agent for treatment of the present invention is extremely preferably used in order to suppress hyperacute rejection upon xenotransplantation of kidney.

By perfusing an organ extracted for organ transplantation with the agent for treatment of the present invention, and further holding and storing the extracted organ in contact with the agent for treatment of the present invention or the like, the α-galactose antigens present on vascular endothelial cells of the organ are eliminated by the action of endo-β-galactosidase, and thus the hyperacute rejection upon transplantation can be suppressed.

Further, the agent for treatment of the present invention can be used for not only an organ already extracted for transplantation, but also an organ to be extracted for transplantation.

For example, an organ may be extracted in the agent for treatment of the present invention by perfusing or filling an organ to be extracted and surrounding thereof with the agent for treatment of the present invention.

The amount of endo-β-galactosidase blended in the agent for treatment of the present invention or the like should be individually determined depending on the method for using the agent for treatment of the present invention, type, size, state, storage time and temperature of an organ to be stored and so forth, and it is not particularly limited. However, about 0.05-5 unit/ml (about 0.005-0.5 mg/ml) in a state of a liquid agent can be exemplified. The definition of "unit" will be described later. In an amount of 0.1-2 unit/ml (about 0.01-0.2 mg/ml) is preferred, and about 0.4-0.5 unit/ml (6.04-0.05 mg/ml) is extremely preferred.

Further, temperature of the agent for treatment of the present invention at the time of organ treatment can also be individually determined depending on the method of use or the like. However, preferred is a temperature at which the agent for treatment of the present invention is not frozen and can be maintained in a solution state, functions of organ can be maintained and enzymatic activity of the endo-β-galactosidase can be maintained. The endo-β-galactosidase C is preferred, because it effectively acts even at a low temperature. In this case, a low temperature, for example, about 4° C., is preferably used.

An organ from which the α-galactose antigens are eliminated (the organ of the present invention) can be obtained by treating an organ expressing the α-galactose antigens with the agent for treatment of the present invention. The expression "α-galactose antigens are eliminated" used herein does not means that all of the α-galactose antigens present in the organ need to be eliminated, but means that the α-galactose antigens may be eliminated to such an extent that hyperacute rejection should not substantially be induced. Specifically, it is preferred that α-galactose antigens present on vascular endothelial cells of an organ are substantially eliminated by perfusing the organ expressing the α-galactose antigens with the agent for treatment of the present invention.

Since no histological change was observed in kidneys treated with the endo-β-galactosidase C as shown in the examples described later, safety of the agent for treatment of the present invention and the organ of the present invention is strongly suggested.

BEST MODE FOR CARRYING OUT THE INVENTION

Figure 1:
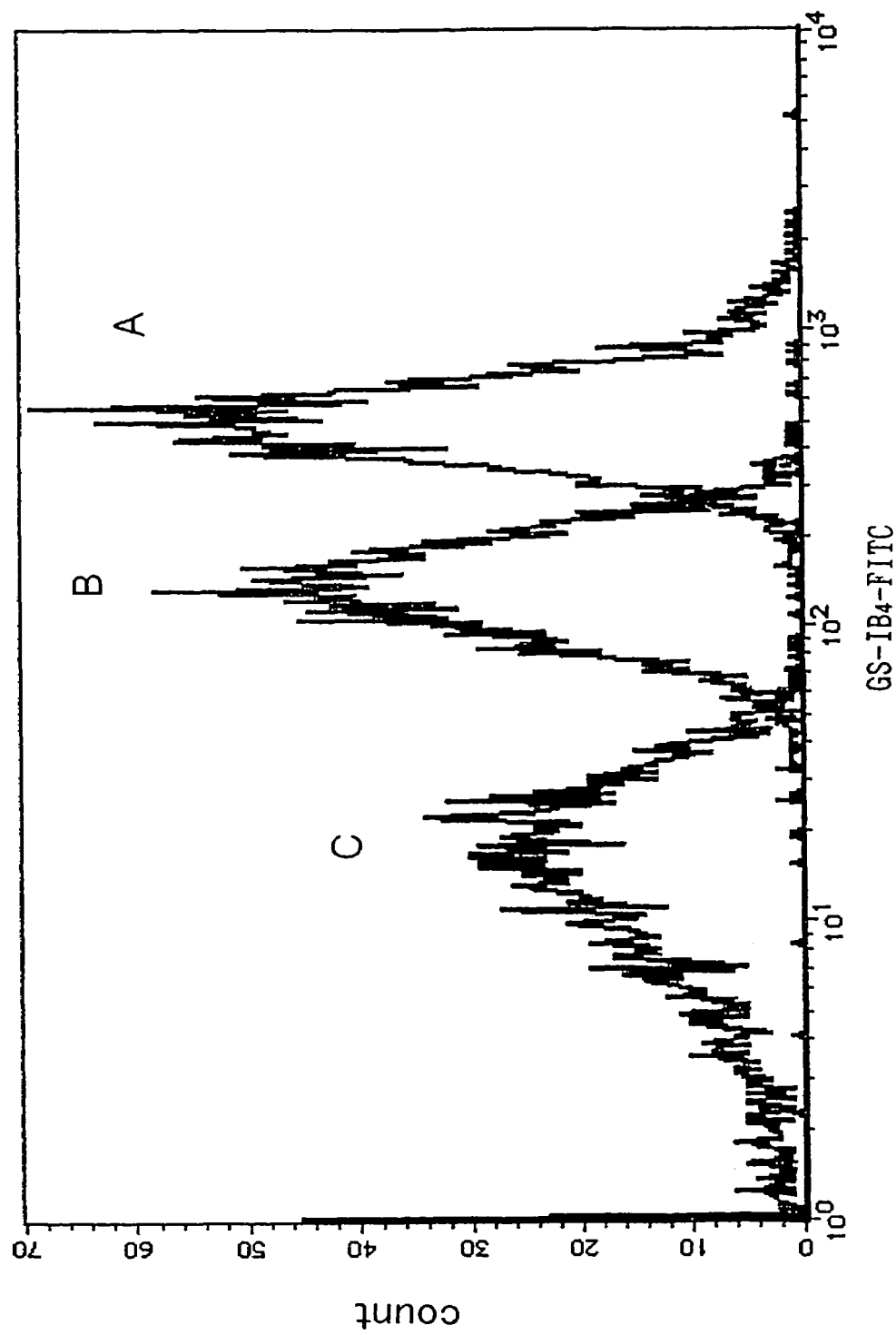
FIG. 1 shows results of analysis of swine erythrocytes treated with endo-β-galactosidase C by using a fluorescent activated cell sorter (FACS).

Hereafter, the present invention will be further specifically explained with reference to the following examples.

<1> Analysis of Partial Amino Acid Sequence of Endo-β-Galactosidase C and Preparation of PCR Primers According to the method described in Japanese Patent Publication No. 7-87783 and J. Biol. Chem., 262, 10086-10092 (1987), proteins were purified from culture broth of *Clostridium perfringens* (ATCC10873, FERM P-8917) by salting out with ammonium sulfate, Sephadex G-200 (Pharmacia) column chromatography and following DEAE-Sephadex A-25 (Pharmacia) column chromatography. The purified proteins were subjected to SDS-polyacrylamide gel electrophoresis (PAGE), and the gel after the electrophoresis was stained with Coomassie Brilliant Blue. A band corresponding to a molecular weight of 90,000 was excised and digested with trypsin, and the digested fragments were separated by high speed liquid chromatography, and partial amino acid sequence of each fragment was analyzed by a protein sequencer ABI 494A (ABI). As a result, the following four kinds of amino acid sequences were obtained.

```
(No. 5)    SEVPSQP                    (SEQ ID NO:3)

(No. 19)   LSDGDLNEEN                 (SEQ ID NO:4)

(No. 42)   QNSDYLIDWI                 (SEQ ID NO:5)

(No. 45)   DENEYVLTNVLNGLIPTTNSK      (SEQ ID NO:6)
```

The following PCR primers were produced based on the above amino sequences.

```
C45-S2 (sense primer)
5'-GAYGARAAYGARTAYGT-3'               (SEQ ID NO:7)

C19-AS1 (antisense primer)
5'-TCYTCRTTNARRTCNCCRTC-3'            (SEQ ID NO:8)
```

2> PCR Using Primers Mentioned Above

PCR (polymerase chain reaction) was performed in a conventional manner by using the aforementioned primers and genomic DNA extracted from *Clostridium perfringens* (ATCC10873, FERM P-8917) as a template. For PCR, following a retention at 94° C. (for 3 minutes), a reaction was performed at 94° C. (for 1 minute)/45° C. (for 1 minute)/72° C. (for 2 minutes) for 35 cycles.

The obtained amplification product was ligated to a cloning vector for nucleotide sequence determination, pGEM-T Easy Vector Systems (Promega), and its nucleotide sequence was analyzed by the dideoxy method using ABI Prism 377 DNA sequencer (ABI). As a result, a partial cDNA (1946 bp) containing sequences that encoded the aforementioned four kinds of amino acid sequences could be obtained.

<3> Cassette PCR Using Partial cDNA Obtained Above

Further, in order to obtain regions on the 5' side and 3' side of the obtained cDNA, cassette PCR was performed by using HindIII-cassette (Takara Shuzo, code number: 3870) for both of the 5' and 3' sides. The primers used for PCR were as follows.

```
(5'-primer)
CP-1:
5'-TGATACTTGTGGTACAGTAGAATGCCCACT-3'  (SEQ ID NO:9)
CP-2:
5'-ATGTTTACTATTAGTAGTAGGTATTAAGCC-3'  (SEQ ID NO:10)

(3'-primer)
CP-3:
5'-AGATGGTATGCATACTAGACCTATGTTCCC-3'  (SEQ ID NO:11)
CP-4:
5'-AAGTTGGAGATGGTTGGGTTGGTGATGTTG-3'  (SEQ ID NO:12)
```

For the cassette PCR, reaction was performed at 94° C. (for 30 seconds)/55° C. (for 2 minute)/72° C. (for 1 minutes) for 30 cycles.

The obtained product was determined for its nucleotide sequence by the same method as described above, and an open reading frame (ORF) consisting of 2535 bp for 845 amino acids was eventually elucidated.

<4> Preparation of Primers for Obtaining Full Length cDNA, Acquisition of Full Length cDNA by PCR and Confirmation of Nucleotide Sequence Full length cDNA was amplified by PCR using the following primers (CP-5 and CP-6) produced based on the information obtained in the above <3>. For PCR, following a retention at 94° C. (for 1 minute) a reaction was performed at 94° C. (for 30 seconds)/55° C. (for 2 minutes)/72° C. (for 1 minute) for 30 cycles.

```
CP-5:
                                          (SEQ ID NO:13)
5'-GCAGCCGAATTCATGAAATTTTTCTCGAAATTCAAAAAGGTA-3'

CP-6:
                                          (SEQ ID NO:14)
5'-GCGTCGCTCGAGTTATTTATTTTGTAAAAAAGTTACTTTAGC-3'
```

The obtained product was ligated to PGEM-T Easy Vector Systems (Promega), and the nucleotide sequence was confirmed by using primers (primers CP-3, CP-5, CP-6 and the following primers).

```
CP-7:
5'-GGTGCAATCTATAATAGGGG-3'       (SEQ ID NO:15)

CP-8:
5'-CCCCTATTATAGATTGCACC-3'       (SEQ ID NO:16)

C5-S1:
5'-AAGTCTGAAGTACCAAGTCA-3'       (SEQ ID NO:17)

CP-11:
5'-GAACTTGTTTGGAGTGACGAG-3'      (SEQ ID NO:18)

M13 Forward:
5'-GTAAAACGACGGCCAGT-3'          (SEQ ID NO:19)

M13 Reverse:
5'-GGAAACAGCTATGACCATG-3'        (SEQ ID NO:20)
```

For the 5' side, 5'-RACE was performed by using CP-1, CP-2 and the following primers, and the nucleotide sequences were confirmed.

```
C5-AS1:  5'-TGACTTGGTACTTCAGACTT-3'   (SEQ ID NO:21)
```

The elucidated nucleotide sequence and amino acid sequence corresponding to it are shown in SEQ ID NO: 1, and only the amino acid sequence is shown in SEQ ID NO: 2, respectively. It was confirmed that the elucidated nucleotide sequence of the DNA of the present invention consisted of ORF consisting 2535 bp for 845 amino acids.

<5> Expression of Enzyme Using cDNA and Assay of Enzymatic Activity (1) Expression of Enzyme cDNA of the coding region was ligated to an EcoRI/XhoI site of pcDSA expression vector incorporated with IgM signal peptide and protein A genes and having SR promoter (FEBS Letters, 360, pp. 1-4 (1995); J. Biol. Chem., 269 (2), pp. 1402-1409 (1994)). The obtained plasmid was transfected into COS-7 cells by using LIPOFECT AMINE PLUS Reagent (Gibco BRL). The transfection was performed in DMEM medium that did not contain FCS.

The cells after the transfection were cultured (10 cm dish× 48) in DMEM medium containing 2% fetal calf serum (FCS) from which IgG was removed by adsorption with Protein A Sepharose CL-4B (Pharmacia). The culture broth was recovered after 3 days, then the cells were cultured in fresh medium for further 5 days, and then the culture broth was recovered.

The recovered culture broth (about 800 ml) was centrifuged at 3000 rpm for 10 minutes, and the supernatant was filtered through a 0.8-μm filter. The filtered supernatant in an amount of 100 ml each was passed through IgG Sepharose 6 Fast Flow (Pharmacia, 6.5 mm×10 mm) to collect the adsorbed fraction. The collected adsorbed fraction was concentrated by using Centricon 10 (Amicon) and stored at −80° C.

(2) Assay of Enzymatic Activity

Sugar chains (galactose antigen) that have the Galα1-3Gal structure and serve as a substrate of endo-β-galactosidase C exist on swine erythrocyte surfaces. By utilizing them, the endo-β-galactosidase C activity was assayed as follows.

(i) Preparation of Swine Erythrocytes

Blood was collected from swine and blood cells were obtained by centrifugation. The blood cells were washed three times with phosphate buffered saline (PBS(−)) containing 0.2% bovine serum albumin (BSA). The washed blood cells were added with 3 mg/ml of dimethyl suberimidate dihydrochloride (DMS, dissolved in a buffer containing 0.1 M $Na_2CO_3$, 0.15 M NaCl and 0.1 mM ethylenediaminetetraacetic acid (EDTA), pH 10.3) and incubated at 37° C. for 20 minutes. Then, the blood cells were washed twice with PBS (−) containing 0.02% EDTA (pH 7.4), and the blood cells were sufficiently suspended in PBS(−) containing 0.2% BSA to prepare 1% blood cell suspension.

(ii) Assay of Enzymatic Activity

The blood cells (50 μl of 1% blood cell suspension) prepared in (i) was put into a tube and centrifuged at 2,000 rpm for 1 minute. The supernatant was removed, and the precipitates (blood cells) was added with and suspended in 100 μl of PBS(−) containing 0.2% BSA, and added with a solution (1 μl or 8 μl) of the enzyme expressed in the above (1) or PBS(−) as a control. Then, the blood cells were incubated at 37° C. for 1 to 2 hours.

After the incubation, the blood cells were washed twice with PBS(−) containing 0.2% BSA and re-suspended in 50 μl of the same buffer. This suspension in an amount of 25 μl was added with 25 μm of FITC (fluorescein isothiocyanate) labeled $GS-IB_4$ (lectin that binds to Galα1-3Gal structure, derived from *Griffonia simplicifolia*, Sigma) diluted 50 times with PBS(−) containing 0.2% BSA, and incubated for 30 minutes under ice cooling. Then, the blood cells were washed with PBS(−) containing 0.2%. BSA, re-suspended in 0.5 ml of the same buffer, and analyzed by a fluorescence activated cell sorter (FACS). The results are shown in FIG. 1.

As a result, when the swine erythrocytes and the expressed enzyme were brought into contact with each other, fluorescence intensity of FITC was decreased (FIG. 1, B) compared with the control (FIG. 1, A). Further, when the amount of the expressed enzyme to be contacted was increased, the fluorescence intensity of FITC was further decreased (FIG. 1, C). This indicated that the expressed enzyme had the endo-β-galactosidase C activity and the binding of the FITC-labeled $GS-IB_4$ to the swine erythrocyte surfaces was decreased as a result of excision of the sugar chains having the Galα1-3Gal structure on the swine erythrocyte surfaces. This result demonstrated that the DNA of the present invention coded for endo-β-galactosidase C actually having the enzymatic activity. Moreover, it was also demonstrated that the recombinant vector of the present invention prepared by using the DNA of the present invention, the transformant of the present invention prepared by using the recombinant vector of the present invention and the production method of the present invention using the transformant of the present invention were actually practical and useful. Furthermore, it was also demonstrated that the α-galactose antigens could be removed by a treatment with endo-β-galactosidase.

<6> Mass Expression of Enzyme Using *Escherichia coli*, Assay of Enzymatic Activity and Application to Xenotransplantation In the following experiments, the enzymatic reaction was performed in 10 μl of 50 mM phosphate buffer (pH 7.2) containing 20 μl of Galα1-3Galβ1-4GlcNAcβ1-3Galβ1-4Glc (Calbiochem). After incubation at 37° C. for 30 minutes, the reaction was terminated by addition of 20 μl of ethanol.

(1) Production of Recombinant Endo-β-Galactosidase C Using *Escherichia coli*

The aforementioned cDNA including the coding region was ligated to an expression vector pFLAG-Shift$_{12}$ (Sigma), which produced a gene product secreted in periplasm. This allows that the enzyme should be expressed as a periplasmic enzyme in *Escherichia coli* (*E. coli*) under control of ompA gene. *E. coli* BL-12 cells were transformed with the above recombinant gene and cultured at 37° C. in 2 L of LB medium containing 50 μl/mL of ampicillin and 0.4% glucose, and 0.1 mM IPTG (isopropyl β-D-thiogalactopyranoside) was added to the medium to induce expression of the enzyme. After 30 minutes, the cells were collected by centrifugation at 5,000×g for 10 minutes, washed twice with 300 mL of Tris-HCl (pH 8.0) at room temperature, and further washed with 300 mL of a solution containing 0.5 M sucrose, 30 mM Tris-HCl (pH 8.0) and 1 mM EDTA.

The cells collected by centrifugation were suspended in 250 mL of pure water cooled with ice so that the enzyme should be released from periplasm. The suspension was centrifuged at 3,500×g for 10 minutes at 4° C. to collect a supernatant containing the released enzyme, and the enzyme fraction was purified by column chromatography using Sephadex G-200 (Pharmacia, 2.7×100 cm) and DEAE-Sephadex A-25 (Pharmacia, 1.0×10 cm) according to the method described in J. Biol. Chem., 262, pp. 10086-10092 (1987). The purified enzyme fraction contained about 700 μg of the protein. The above procedure was repeated to produce a large amount of the enzyme.

The purified enzyme fraction was analyzed by SDS-polyacrylamide gel electrophoresis (SDS-PAGE, 8% gel). As a result, a major band having an apparent molecular weight of 95 kDa and a minor band (97 kDa) adjacent to the major band were identified. The N-terminus amino acid sequence of the major band (95 kDa) was analyzed and found to be DENEYVL (in single letter code, equivalent to the amino acid numbers 35-41 in SEQ ID NO: 2). Moreover, a cluster of hydrophobic amino acids typically found in a signal sequence existed in the segment of the amino acid numbers 1-34 in SEQ ID NO: 2. Based on these, it is thought that the segment of the amino acid numbers 1-34 in SEQ ID NO: 2 should be a signal sequence, and it is thought that the major band (95 kDa) is a protein lacking in that signal sequence (protein having an amino acid sequence represented by the amino acid numbers 35-845 in SEQ ID NO: 2). Further, based on the difference of the molecular weights, it is considered that the minor band (97 kDa) is a protein having a signal sequence.

(2) Assay of Endo-β-Galactosidase C

The enzymatic reaction was performed by using 4 mU of endo-β-galactosidase C in the same manner as described above.

After the reaction was terminated, the solution after the reaction was desalted with Dowex 50 W×2H$^+$ form and 1×2 acetate form, and then 1/10 amount of hydrolysate was spotted on a Silica Gel 60 TLC plate (Merck).

Thin layer chromatography (TLC) was performed for the plate by development with n-propanol:ethyl acetate:H$_2$O (7:2:1), and the plate was sprayed with orcinol-sulfuric acid reagent and heated so that spots of sugars should emerge (J. Neurochem., 1, pp. 42-53 (1956)). The amounts of the released products were determined by a densitometer (Gel Doc 1000, BIO-RAD). Under this assay condition, the enzymatic activity is proportional to the amount of the enzyme and reaction time until 40% of the substrate is hydrolyzed. Further, enzymatic activity of "1 Unit" is defined as an amount of the enzyme required for hydrolyzing 1 μmole of the substrate in 1 minute under the aforementioned conditions of the enzymatic reaction.

As a result, the recombinant enzyme obtained in the aforementioned (1) hydrolyzed the pentasaccharide (Galα1-3Galβ1-4GlcNAcβ1-3Galβ1-4Glc) and released two kinds of oligosaccharides, which were separated by TLC.

Then, in order to identify these oligosaccharides, electrospray mass spectrometry was performed.

Galα1-3Galβ1-4GlcNAcβ1-3Galβ1-4Glc (20 μg) was hydrolyzed with 4 mU of the enzyme at 37° C. for 30 minutes in 10 μl of 30 mM NaCl. After the enzymatic reaction was terminated with 20 μl of ethanol, the reaction mixture was mixed with 1.5-fold amount of 83% acetonitrile containing 17 mM ammonium acetate. The mass spectrometry was performed by using a triple quadrupole mass spectrometer, API 300 (Perkin Elmer Sciex Instruments), equipped with an electrospray ion source. A sample was directly injected into the electrosptay ion source at a flow rate of 0.3 ml/hour. The spray was obtained with a potential difference of 4.8 kV.

As a result, m/z of 892.2 was obtained as the result of analysis of the pentasaccharide before the enzymatic digestion. This value corresponds to a number obtained by adding 23 to the theoretical molecular weight of the pentasaccharide, and it is thought that the value was obtained due to addition of Na$^+$ ion. As a result of analysis of the oligosaccharides after the enzymatic digestion, two of marked peaks were obtained at positions of m/z=568.1 and m/z=365.0. The former mass corresponds to that obtained by adding Na$^+$ to GlcNAcβ1-3Galβ1-4Glc, and the latter mass corresponds to that obtained by adding Na$^+$ to Galα1-3Gal.

Based on these results, it was confirmed that the cloned enzyme should be endo-β-galactosidase C and it should hydrolyze the Galβ1-4GlcNAc linkage to release Galα1-3Gal disaccharide. Moreover, this enzyme showed a specific activity of 10.5 U/mg protein, and thus it was demonstrated that the enzyme had strong activity. The protein amount of the purified enzyme was determined by using Micro BCA protein assay reagent kit (Pierce) and bovine serum albumin as a standard.

Further, contamination of other glycosidases in the purified enzyme fraction was determined by using a p-nitrophenyl glycoside for each enzyme as a substrate, which was incubated with 29.4 μg of the purified enzyme at 37° C. for 1 hour in 0.2 mL of a reaction mixture at pH 7.0 (50 mM phosphate buffer) and pH 6.0 (50 mM citrate-phosphate buffer). Further, contamination of proteases was similarly determined by the method described in J. Biochem., 75, pp. 707-714 (1974) under the conditions of pH 7.0 and pH 6.0.

As a result, the purified enzyme fraction did not substantially contain any of protease, α-galactosidase, β-galactosidase and β-N-acetylglucosaminidase. Moreover, this recombinant enzyme showed an optimum pH in the range of 7.0-

8.0, and it was the same as the optimum pH of the enzyme obtained from culture broth of *C. perfringens* (J. Biol. Chem., 262, pp. 10086-10092 (1987)). Furthermore, enzymatic activity of this enzyme at 4° C. was about 40% of the activity at 37° C.

(3) Application to Xenotransplantation

In the following descriptions, "PBS/BSA" means PBS(−) containing 0.2% BSA.

(3-1) Removal of α-Galactose Antigens from Viable Cells

Swine erythrocytes were prepared in the same manner as in the above <5>. Swine vascular endothelial cells were isolated from swine by the method described in Transplantation, 62, pp. 105-113 (1996). These cells were collected with Trypsin-EDTA (Gibco BRL), washed twice with PBS/BSA, and suspended in PBS/BSA again. The endo-β-galactosidase C obtained in the above (1) (70 mU in 7 μl of PBS) was added to the vascular endothelial cells ($2\times10^5$ cells/50 μl), and the enzymatic reaction was performed at 37° C. for 1 hour.

After the enzymatic reaction, the erythrocytes or the endothelial cells were washed twice with PBS/BSA and allowed to react with FITC-labeled $GS-IB_4$ or human blood serum. In the case of the former, the cells were suspended in 50 μl of PBS/BSA containing 1 μl of FITC-$GS-IB_4$ (Sigma) and maintained for 30 minutes under ice cooling. In the case of the latter, the washed cells were incubated with 100 μl of normal human serum collected from 50 of healthy volunteers and pooled (diluted with PBS/BSA at a ratio of 1:1). After incubation for 30 minutes under ice cooling, the cells were washed twice with PBS/BSA and incubated with 100 μl of FITC-conjugated rabbit anti-human IgG, IgM or IgA (Dako, each diluted with PBS/BSA at a ratio of 1:20) for 30 minutes under ice cooling. FITC-conjugated mouse monoclonal anti-human $IgG_1$ (Zymed), $IgG_2$, $IgG_3$ or $IgG_4$ (Sigma) was also used.

The stained erythrocytes or endothelial cells were washed twice with PBS/BSA, suspended in 0.5 mL of PBS/BSA, and analyzed by FACS (FACS Calibur, Becton Dickinson).

(3-2) Assay of Complement-Dependent Cytotoxicity

The swine vascular endothelial cells were inoculated onto a 96-well culture plate in an amount of $1\times10^4$ cells/well one day before the assay. The cells were washed with PBS(−) and then incubated at 37° C. in 50 μl of Dulbecco's modified Eagle medium containing 70 mU of endo-β-galactosidase C obtained in the above (1) for 2 hours. The control cells were incubated under no enzyme condition. The cells were washed twice and incubated at 37° C. for 1 hour with 25% or 50% of normal human serum (50 μl) diluted with PBS(−). As for the human blood serum, one collected from 10 of healthy volunteers and pooled was used. After incubation, survival of the cells was determined by an assay utilizing 3-(4,5-dimethylthiazol-2-yl)-2,5-diphenyltetrazolium bromide (MTT, Sigma) according to the method described in Biochem. Biophys. Res. Comm., 232, pp. 731-736 (1997). Absorbance was measured at 540 nm for each well by using an automatic plate reader (EAR340, SLT-Labinstruments) and defined as "survival of cells under existence of complements". "Survival of cells under absence of complement" was also determined for each assay by using blood serum that was treated at 56° C. for 30 minutes to inactivate the complement. The complement-dependent cytotoxicity was calculated according to the following equation. The experiments were performed in triplicate.

% Cytotoxicity=[(Survival of cells under absence of complement−Survival of cells under existence of complement)/Survival of cells under absence of complement]×100

Figure 2:
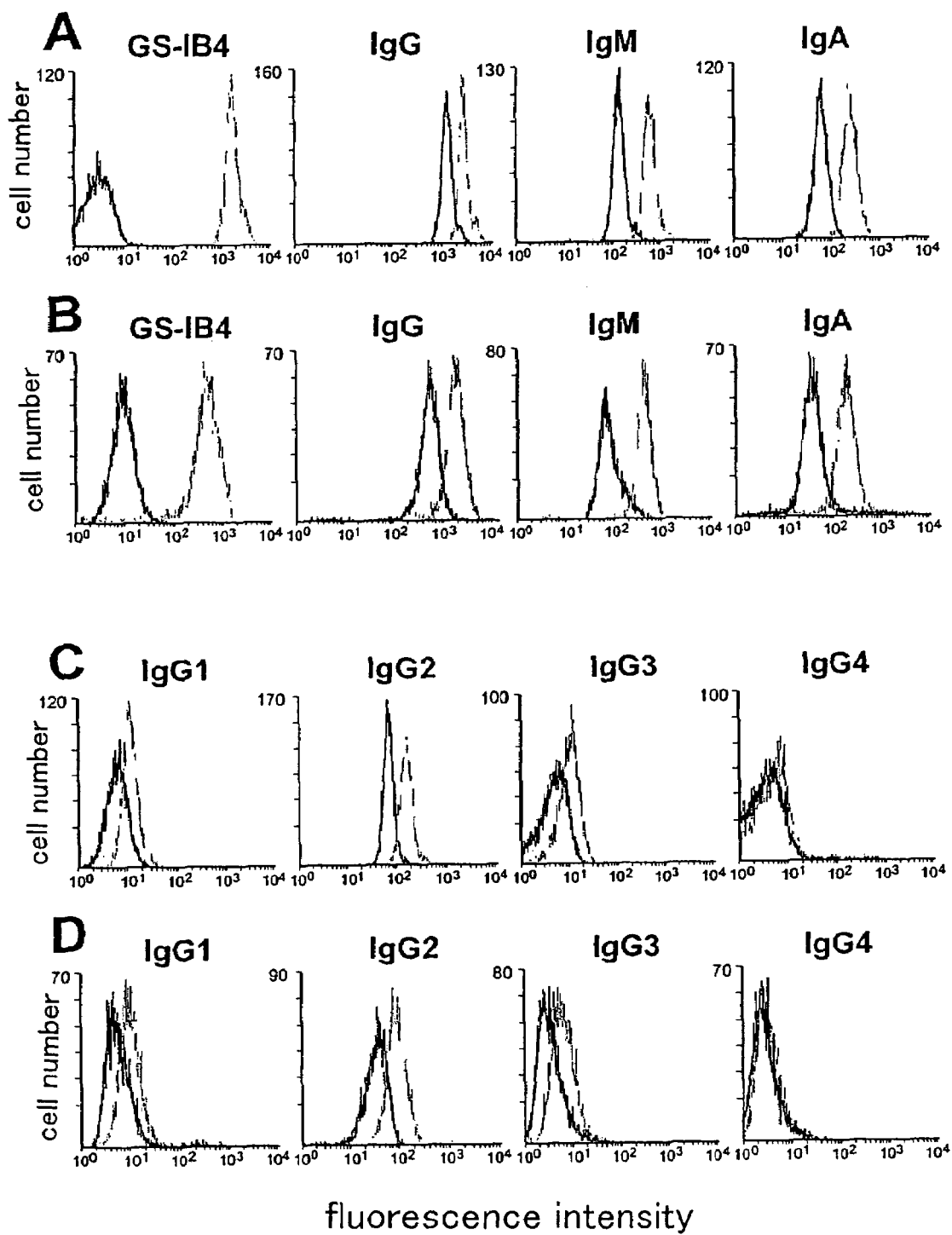
FIG. 2 shows decreases in binding properties of GS-IB$_4$ and human immunoglobulin to swine cells treated with endo-β-galactosidase C.
Figure 3:
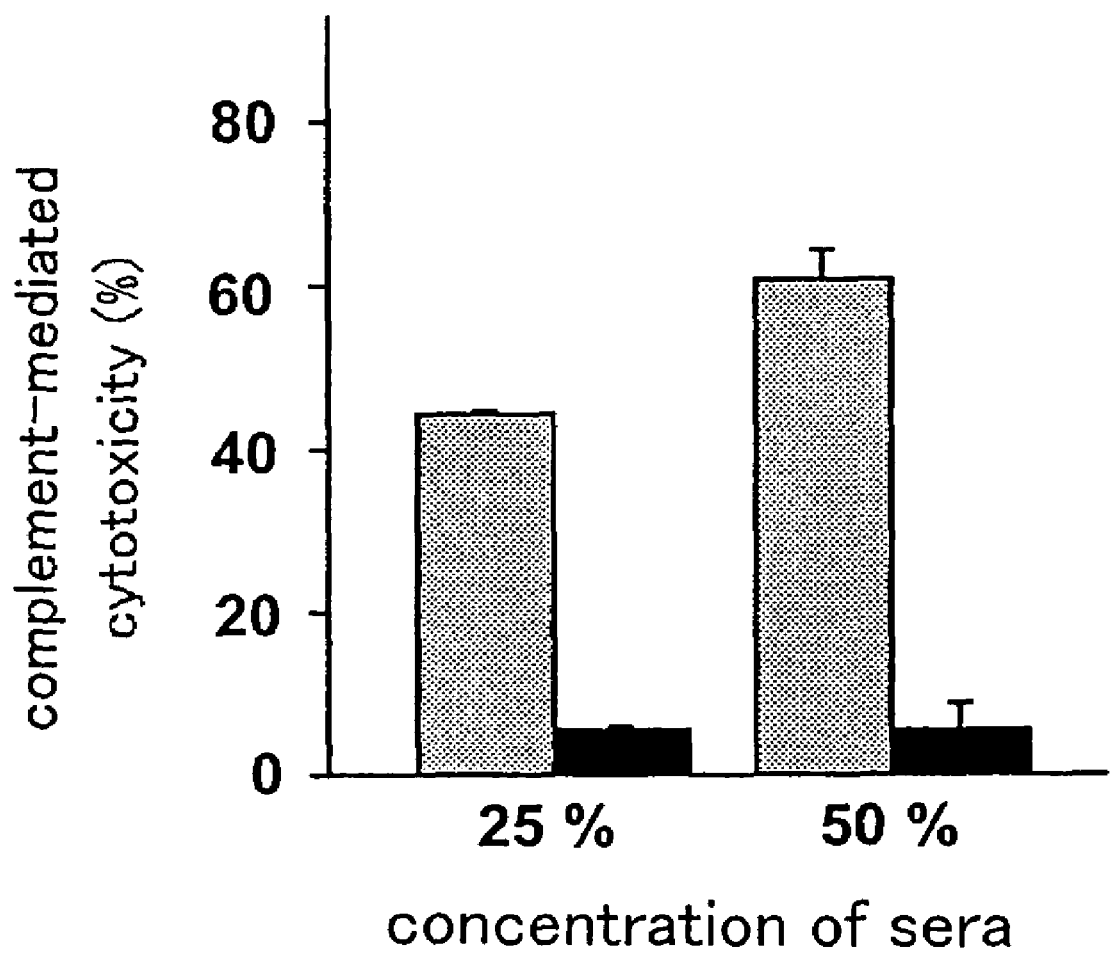
FIG. 3 shows an effect of endo-β-galactosidase C on complement-dependent cytotoxicity.

The results of the above experiments are shown in FIGS. 2 and 3.

FIG. 2 shows attenuations of the properties of $GS-IB_4$ and human immunoglobulin for binding to the swine cells treated with the recombinant endo-β-galactosidase C. A and C show the results of the experiments using erythrocytes, and B and D show the results of the experiments using vascular endothelial cells. The thick lines in the figures represent the results obtained after the enzyme treatment, and normal lines represent the results obtained before the enzyme treatment.

Further, FIG. 3 shows the effect of endo-β-galactosidase C on the complement-dependent cytotoxicity. In FIG. 3, the hatched bars represent the results obtained without the enzymatic treatment, and the black bars represents the results obtained with enzymatic treatment, respectively. Averages of results of assays performed in triplicate are shown with standard errors.

After the treatment with the recombinant endo-β-galactosidase C, 99% or more of α-galactose antigens (recognized by FITC-$GS-IB_4$) were removed from the swine erythrocytes (FIG. 2A). Similarly, 98% of the α-galactosyl epitopes were enzymatically removed from the swine vascular endothelial cells (FIG. 2B). The binding of IgM to erythrocytes treated with the enzyme was decreased to 25% of the cells that were not treated (FIG. 2A). Moreover, as for the endothelial cells, it decreased to 23% or less (FIG. 2B). The binding of IgA and IgG in human blood serum to the endothelial cells treated with the enzyme similarly decreased to 21% and 33%, respectively (FIG. 2B). There was comparatively little decrease of the binding of IgG to erythrocytes treated with the enzyme (FIG. 2A).

Furthermore, as a result of use of antibodies to human IgG subclass, the bindings of $IgG_1$, $IgG_2$ and $IgG_3$ to the treated cells were markedly decreased (FIGS. 2C and 2D). On the other hand, the binding of $IgG_4$ did not change. The cells treated with endo-β-galactosidase C showed decreased sensitivity to the complement-dependent cytotoxicity caused by human blood serum (FIG. 3).

(3-3) Treatment of Swine Renal Vessel with Endo-β-Galactosidase C by ex Vivo Perfusion Kidneys were extracted by a usual surgical procedure from female swine obtained by heterogenous mating of Landrace/Yorkshire (Oguri Chikusan, body weight of 10-12 kg) after perfusion of the kidneys with physiological saline and University of Wisconsin (UW) solution (Transplantation, 45, pp. 673-676 (1988)). Right kidneys were perfused ex vivo twice with a flow of 100 mL of cold UW solution containing 45.1 units of endo-β-galactosidase C formed by gravity (1×g). Perfusion of left kidneys was performed without the enzyme. The kidneys of the both sides were stored at 4° C. in the perfusates for 4 hours. A lower temperature is preferred for storage of tissues and the endo-β-galactosidase C effectively act also at a low temperature. Therefore, the reaction was allowed at 4° C.

Biopsy was performed immediately after the points 1 hour and 4 hours after the perfusion. Subsequently, each kidney was perfused twice with 100 mL of fresh frozen human plasma collected from 3 of healthy volunteers.

For histological study, each sample obtained by the biopsy was fixed with formalin, and stained by hematoxylin/eosine and periodic acid-Schiff staining. The sample was immediately frozen again in liquid nitrogen, stained with FITC-$GS-IB_4$, and observed with a fluorescence microscope.

In this observation, it was confirmed that α-galactose antigens that had existed in the lumens of vascular endothelial cells were actually removed by the enzymatic reaction at 4° C.

for 4 hours through the staining with FITC-GS-IB$_4$. Any histological change was not observed for kidneys treated with the enzyme.

Furthermore, the human plasma used for the perfusion was collected, and the level of remaining immunoglobulin was analyzed by using the aforementioned swine erythrocytes in FACS.

This was done in order to investigate whether the binding of immunoglobulin in human plasma to vessels treated with the enzyme was decreased by the above method of removing α-galactose antigens in situ as in the case of vascular endothelial cells or erythrocytes. Although it is possible to quantitatively determine separated cells by using FACS, it is not easy to directly measure the amount of immunoglobulin binding in an intact vessel. Therefore, it was decided to measure decrease of the binding activity of immunoglobulin to swine erythrocytes after the perfusion of the kidneys. In order to prevent dispersion among swine individuals, two kidneys extracted from the same individual were used. The right kidney was treated with endo-β-galactosidase C, and the left kidney was perfused with a solution not containing the enzyme. Subsequently, perfusion was performed with human plasma (100 mL) under gravity.

Figure 4:
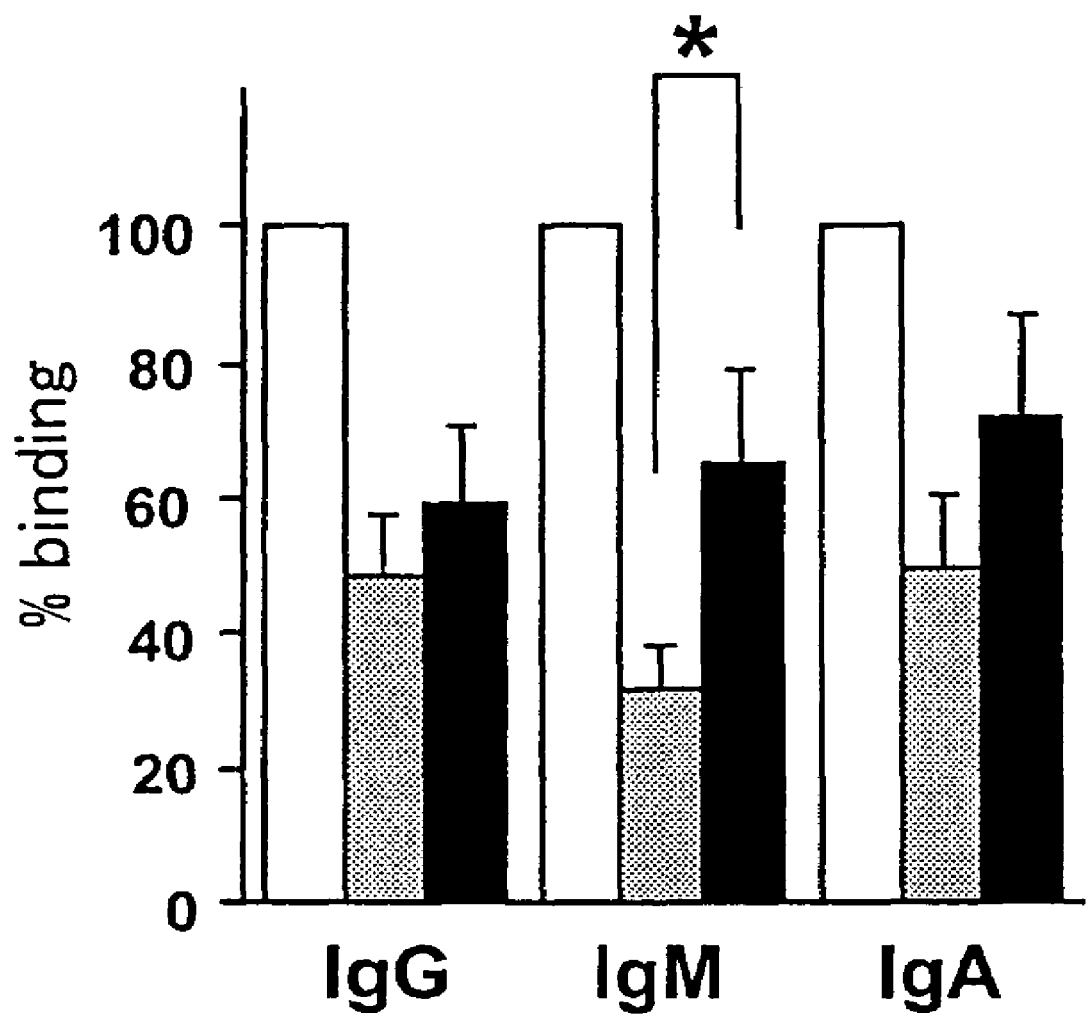
FIG. 4 shows decreases in adsorption properties of immunoglobulins in human plasma to swine renal blood vessels treated with endo-β-galactosidase C.

The perfused human plasma was collected, allowed to react with swine erythrocytes, and then allowed to react with FITC-conjugated antibodies directed to human immunoglobulin. The stained erythrocytes were analyzed by FACS. The results are shown in FIG. 4. The results are shown with relative values based on the average fluorescence intensity obtained in the case utilizing the plasma before the perfusion, which was taken as 100%.

In FIG. 4, the white bars indicate the results obtained by using the plasma before the perfusion, the hatched bars indicate the results obtained when the perfusion was performed only with a solution not containing the enzyme, and the black bars indicate the results obtained when the perfusion was performed with a solution containing the enzyme, respectively. Averages of the results obtained in independent three experiments are shown with standard errors. The results were analyzed by the Student's T-test. The symbol "*" in FIG. 4 represents significance with $p<0.05$.

As a result, it was found that the binding amount of IgM was smaller in the kidney treated with the enzyme than that in the kidney treated with a solution not containing the enzyme. In the swine kidneys that were not treated with the enzyme, 31% of IgM binding activity remained in the human plasma on average (FIG. 4). On the other hand, in the kidneys treated with the enzyme, 64% of the activity remained on average (FIG. 4). This difference was statistically significant. These results indicate that a large amount of IgM-binding antigen epitopes were removed by the endo-β-galactosidase C digestion.

However, the binding abilities of IgG and IgA were not decreased so much by the enzymatic treatment, and did not show a statistically significant difference, either (FIG. 4).

INDUSTRIAL APPLICABILITY

By using the DNA of the present invention, endo-β-galactosidase C can be prepared by a genetic engineering technique at a low cost and in a large amount.

Moreover, the recombinant vector of the present invention prepared by using the DNA of the present invention, the transformant of the present invention prepared by using the recombinant vector of the present invention and the production method of the present invention utilizing the transformant of the present invention are useful for extensive preparation of endo-β-galactosidase C.

Furthermore, if the regent for treatment of the present invention is used to preliminarily remove α-galactose antigens expressed in, for example, organs of swine or the like and this organ is used for transplantation into human, ape or the like (not expressing the α-galactose antigens), hyperacute rejection in the case of xenotransplantation can be suppressed, and therefore it is extremely useful. It is particularly useful for treatment of such a kidney for transplantation.

The organ of the present invention obtained by treating an organ with the regent for treatment of the present invention is extremely useful as an organ for xenotransplantation.

SEQUENCE LISTING

```
<160> NUMBER OF SEQ ID NOS: 21

<210> SEQ ID NO 1
<211> LENGTH: 3013
<212> TYPE: DNA
<213> ORGANISM: Clostridium perfringens
<220> FEATURE:
<221> NAME/KEY: CDS
<222> LOCATION: (246)...(2780)

<400> SEQUENCE: 1
aagcttttaa atcatgccaa tgaaggaaag gaaagagtaa agttatttgg attagacaaa      60
gatggggatt ataagttgag ttacccttat gaaaaagaat ttaagggtga tgaacttatg     120
aatgttggaa tttcaatgaa tgatgattat ttttgtaata gcggaaatga tttttcatca     180
gtactttatt tattaagaaa aatataaatt taatatattt taataattaa aggaggaatc     240 tgtat atg aaa ttt ttc tcg aaa ttc aaa aag gta aac gta ttt ctt att    290
      Met Lys Phe Phe Ser Lys Phe Lys Lys Val Asn Val Phe Leu Ile
        1               5                  10                  15 tta ttt gct ttt ata ggt aca att ttc ttg agt agt ttt agt aaa tta    338
Leu Phe Ala Phe Ile Gly Thr Ile Phe Leu Ser Ser Phe Ser Lys Leu
                 20                  25                  30
```

| | | |
|---|---|---|
| gtt tta gct gat gag aat gaa tat gta ctt aca aat gta tta aat ggc<br>Val Leu Ala Asp Glu Asn Glu Tyr Val Leu Thr Asn Val Leu Asn Gly<br>                35                        40                        45 | 386 |
| tta ata cct act act aat agt aaa cat atg att att agt ggg cat tct<br>Leu Ile Pro Thr Thr Asn Ser Lys His Met Ile Ile Ser Gly His Ser<br>        50                        55                        60 | 434 |
| act gta cca caa gta tca ata tta cat cca gat tca gca act gat gga<br>Thr Val Pro Gln Val Ser Ile Leu His Pro Asp Ser Ala Thr Asp Gly<br>        65                        70                        75 | 482 |
| gat aat tca tct agt aat gat gat agt tta aat act aaa gtt ata gtt<br>Asp Asn Ser Ser Ser Asn Asp Asp Ser Leu Asn Thr Lys Val Ile Val<br>80                        85                        90                        95 | 530 |
| gga gaa gaa aca gga gga tta gat aat ggt tat agt aaa tgg gaa cct<br>Gly Glu Glu Thr Gly Gly Leu Asp Asn Gly Tyr Ser Lys Trp Glu Pro<br>                    100                       105                      110 | 578 |
| gtt ttt cta caa tat gat tta aaa aaa att cgt cca gta aaa gaa atc<br>Val Phe Leu Gln Tyr Asp Leu Lys Lys Ile Arg Pro Val Lys Glu Ile<br>                  115                       120                      125 | 626 |
| aaa att tat aga aat act tat gat aat gca ata tca aca ttc aaa gat<br>Lys Ile Tyr Arg Asn Thr Tyr Asp Asn Ala Ile Ser Thr Phe Lys Asp<br>            130                       135                      140 | 674 |
| gta aaa gta gaa tta tca act agt cca aat ttt gaa aaa gat aat aca<br>Val Lys Val Glu Leu Ser Thr Ser Pro Asn Phe Glu Lys Asp Asn Thr<br>        145                        150                       155 | 722 |
| tct gtt gtg ttt gaa aag caa gat att att gaa agt aga gaa agc aaa<br>Ser Val Val Phe Glu Lys Gln Asp Ile Ile Glu Ser Arg Glu Ser Lys<br>160                    165                       170                      175 | 770 |
| ggt aat cct caa att ata agt tta gat aaa gct att gat gct caa tat<br>Gly Asn Pro Gln Ile Ile Ser Leu Asp Lys Ala Ile Asp Ala Gln Tyr<br>                  180                       185                      190 | 818 |
| atc cga att tgg gga aag gga cat tat att gaa aat acc aat agt tca<br>Ile Arg Ile Trp Gly Lys Gly His Tyr Ile Glu Asn Thr Asn Ser Ser<br>            195                       200                      205 | 866 |
| tgg aaa gga tat agc aat gga aat ctt tat aat gaa ata gaa gtt atg<br>Trp Lys Gly Tyr Ser Asn Gly Asn Leu Tyr Asn Glu Ile Glu Val Met<br>        210                        215                       220 | 914 |
| gct aat gtt cca aag tct gaa gta cca agt cag cca gac aat att cag<br>Ala Asn Val Pro Lys Ser Glu Val Pro Ser Gln Pro Asp Asn Ile Gln<br>225                    230                       235 | 962 |
| cct aga aat cta gca agt gga aag ctt ccg tat gtt tat gga tta gag<br>Pro Arg Asn Leu Ala Ser Gly Lys Leu Pro Tyr Val Tyr Gly Leu Glu<br>240                    245                       250                      255 | 1010 |
| cca agt aat ata gaa gca att aca gat gga aaa ata gat gat aat tat<br>Pro Ser Asn Ile Glu Ala Ile Thr Asp Gly Lys Ile Asp Asp Asn Tyr<br>                  260                       265                      270 | 1058 |
| gct gta cac aat agt atg gga aat aac tgg ctt caa ttt gaa tat aaa<br>Ala Val His Asn Ser Met Gly Asn Asn Trp Leu Gln Phe Glu Tyr Lys<br>            275                       280                      285 | 1106 |
| aat act tat aaa ttt aat agt ata aag ttt aaa tta gaa cca ggg aac<br>Asn Thr Tyr Lys Phe Asn Ser Ile Lys Phe Lys Leu Glu Pro Gly Asn<br>        290                        295                       300 | 1154 |
| tat aaa tct gtt aaa gta gct att tct aat tct cca aac aat gga ttt<br>Tyr Lys Ser Val Lys Val Ala Ile Ser Asn Ser Pro Asn Asn Gly Phe<br>305                    310                       315 | 1202 |
| aaa gag gtt ttt agt aaa ata aat tgg aca caa aat aat gat tta gaa<br>Lys Glu Val Phe Ser Lys Ile Asn Trp Thr Gln Asn Asn Asp Leu Glu<br>320                    325                       330                      335 | 1250 |
| gta ata aat tta cct tct aat act aaa ggc aga tat att cgt ttt aca<br>Val Ile Asn Leu Pro Ser Asn Thr Lys Gly Arg Tyr Ile Arg Phe Thr<br>            340                       345                      350 | 1298 |

-continued

```
att gat aaa gat gga aag agt aaa aca aaa tat tct gag att gaa ata     1346
Ile Asp Lys Asp Gly Lys Ser Lys Thr Lys Tyr Ser Glu Ile Glu Ile
            355                 360                 365 tgg gga aca gga aat aat tat gat gaa agt aaa gat gag tac gtt gaa     1394
Trp Gly Thr Gly Asn Asn Tyr Asp Glu Ser Lys Asp Glu Tyr Val Glu
        370                 375                 380 cca caa tcc aaa tat aat gaa ctt gtt tgg agt gac gag ttt aat ggt     1442
Pro Gln Ser Lys Tyr Asn Glu Leu Val Trp Ser Asp Glu Phe Asn Gly
    385                 390                 395 gaa aaa ata gat gag aat aaa tgg act att ata gat gga atg gtt aac     1490
Glu Lys Ile Asp Glu Asn Lys Trp Thr Ile Ile Asp Gly Met Val Asn
400                 405                 410                 415 cat ggt gca atc tat aat agg gga gca gta agc ata aaa aag gat ggc     1538
His Gly Ala Ile Tyr Asn Arg Gly Ala Val Ser Ile Lys Lys Asp Gly
                420                 425                 430 aat aat agc tat tta gca ata aac act aaa aac ttt aat agc aca gaa     1586
Asn Asn Ser Tyr Leu Ala Ile Asn Thr Lys Asn Phe Asn Ser Thr Glu
            435                 440                 445 gaa tta att aag gct gtt gga gta gat aat tat tta gga caa agt ata     1634
Glu Leu Ile Lys Ala Val Gly Val Asp Asn Tyr Leu Gly Gln Ser Ile
        450                 455                 460 aat aaa caa aaa gtt act tgg tca tct gga aga att gaa tca aaa aat     1682
Asn Lys Gln Lys Val Thr Trp Ser Ser Gly Arg Ile Glu Ser Lys Asn
    465                 470                 475 aaa tat tct ttt caa ttt gga cgt atg gca gta agg gca aaa gta aat     1730
Lys Tyr Ser Phe Gln Phe Gly Arg Met Ala Val Arg Ala Lys Val Asn
480                 485                 490                 495 gat tct caa gga att tgg cca gca ata tgg atg tta tct caa gat gaa     1778
Asp Ser Gln Gly Ile Trp Pro Ala Ile Trp Met Leu Ser Gln Asp Glu
                500                 505                 510 aca ggc cat gat gaa ata gat gtt tta gaa tat tta gga caa gat cct     1826
Thr Gly His Asp Glu Ile Asp Val Leu Glu Tyr Leu Gly Gln Asp Pro
            515                 520                 525 tgg ggt gca tgg aca act aat cat ttt gga ata tta gga aaa aat aaa     1874
Trp Gly Ala Trp Thr Thr Asn His Phe Gly Ile Leu Gly Lys Asn Lys
        530                 535                 540 gct tct aat gga att aga aat agt aat tat gag gct tgg agt caa gat     1922
Ala Ser Asn Gly Ile Arg Asn Ser Asn Tyr Glu Ala Trp Ser Gln Asp
    545                 550                 555 ttt cat gtc ttt gaa gtt gaa tgg gat cca gaa ttt ata aaa tgg tat     1970
Phe His Val Phe Glu Val Glu Trp Asp Pro Glu Phe Ile Lys Trp Tyr
560                 565                 570                 575 ata gat gga aag gaa gta ttt caa agt act caa gga aga gat gat ggc     2018
Ile Asp Gly Lys Glu Val Phe Gln Ser Thr Gln Gly Arg Asp Asp Gly
                580                 585                 590 aga gat ggt atg cat act aga cct atg ttc cca ata tta gag aca caa     2066
Arg Asp Gly Met His Thr Arg Pro Met Phe Pro Ile Leu Glu Thr Gln
            595                 600                 605 gtt gga gat ggt tgg gtt ggt gat gtt gat tat aat aag caa aat aca     2114
Val Gly Asp Gly Trp Val Gly Asp Val Asp Tyr Asn Lys Gln Asn Thr
        610                 615                 620 aag caa aat tca gat tat tta att gat tgg ata aga gta tat caa atg     2162
Lys Gln Asn Ser Asp Tyr Leu Ile Asp Trp Ile Arg Val Tyr Gln Met
    625                 630                 635 cct aat caa gca aat gta aaa ttt gat gat tta aga agt ctt gat aag     2210
Pro Asn Gln Ala Asn Val Lys Phe Asp Asp Leu Arg Ser Leu Asp Lys
640                 645                 650                 655 aaa gaa aat aaa gga tat gaa gta act cct tat tct cat aca aat aat     2258
Lys Glu Asn Lys Gly Tyr Glu Val Thr Pro Tyr Ser His Thr Asn Asn
                660                 665                 670
```

-continued

```
tta ata aaa tta tca gat gga gat tta aat gaa gaa aac aag gat aat    2306
Leu Ile Lys Leu Ser Asp Gly Asp Leu Asn Glu Glu Asn Lys Asp Asn
            675                 680                 685 ttt tac tat ggg ggt caa cct aga tta gaa aat aat cgt ata gct gtt    2354
Phe Tyr Tyr Gly Gly Gln Pro Arg Leu Glu Asn Asn Arg Ile Ala Val
        690                 695                 700 gga gaa aat gga ggt aga gaa tct ata att tat aat gtt act aat gtt    2402
Gly Glu Asn Gly Gly Arg Glu Ser Ile Ile Tyr Asn Val Thr Asn Val
705                 710                 715 aaa gat ata cat tta act act tac tat caa act att gaa gat aaa atc    2450
Lys Asp Ile His Leu Thr Thr Tyr Tyr Gln Thr Ile Glu Asp Lys Ile
720                 725                 730                 735 aca tgg aat aga agt gca ggt gca tat gaa gga tat tca att aga tca    2498
Thr Trp Asn Arg Ser Ala Gly Ala Tyr Glu Gly Tyr Ser Ile Arg Ser
            740                 745                 750 tca tta ata agt ggt aat ata gat ttt aaa tta ttt aca tca gat gac    2546
Ser Leu Ile Ser Gly Asn Ile Asp Phe Lys Leu Phe Thr Ser Asp Asp
        755                 760                 765 gga gaa att tgg aat gaa gtt aga aat gta aaa ata gta gat aat ttt    2594
Gly Glu Ile Trp Asn Glu Val Arg Asn Val Lys Ile Val Asp Asn Phe
770                 775                 780 gta gaa aaa cat cca gga tat gcc aga aca aca ttt gat gct tat aat    2642
Val Glu Lys His Pro Gly Tyr Ala Arg Thr Thr Phe Asp Ala Tyr Asn
785                 790                 795 tta cca aag aat act caa ttt ata aaa att gaa ttt cca caa tat aaa    2690
Leu Pro Lys Asn Thr Gln Phe Ile Lys Ile Glu Phe Pro Gln Tyr Lys
800                 805                 810                 815 aat gta aaa tat aga tta aat agt ggg gct ata aaa gat gtg aaa aat    2738
Asn Val Lys Tyr Arg Leu Asn Ser Gly Ala Ile Lys Asp Val Lys Asn
            820                 825                 830 act gat att caa tta gct aaa gta act ttt tta caa aat aaa           2780
Thr Asp Ile Gln Leu Ala Lys Val Thr Phe Leu Gln Asn Lys
            835                 840                 845 taaaataact tcactcaaaa ttttatttga taattttgag tgaagttatt cattataaga    2840
ccatatgatt aatattataa tgttttaaga tcagtttata aaaggagttt agagttatta    2900
taagtaaatg acagtaagta aaaaaaatag tatacttaat taaattggtt atttaaaatt    2960
attaaattgt atggagggta aaatatgagt aatttagatt gttttttaag ctt           3013
```

<210> SEQ ID NO 2
<211> LENGTH: 845
<212> TYPE: PRT
<213> ORGANISM: Clostridium perfringens

<400> SEQUENCE: 2

```
Met Lys Phe Phe Ser Lys Phe Lys Lys Val Asn Val Phe Leu Ile Leu
1               5                   10                  15

Phe Ala Phe Ile Gly Thr Ile Phe Leu Ser Ser Phe Ser Lys Leu Val
            20                  25                  30

Leu Ala Asp Glu Asn Glu Tyr Val Leu Thr Asn Val Leu Asn Gly Leu
        35                  40                  45

Ile Pro Thr Thr Asn Ser Lys His Met Ile Ile Ser Gly His Ser Thr
    50                  55                  60

Val Pro Gln Val Ser Ile Leu His Pro Asp Ser Ala Thr Asp Gly Asp
65                  70                  75                  80

Asn Ser Ser Ser Asn Asp Asp Ser Leu Asn Thr Lys Val Ile Val Gly
                85                  90                  95
```

-continued

```
Glu Glu Thr Gly Gly Leu Asp Asn Gly Tyr Ser Lys Trp Glu Pro Val
            100                 105                 110
Phe Leu Gln Tyr Asp Leu Lys Lys Ile Arg Pro Val Lys Glu Ile Lys
            115                 120                 125
Ile Tyr Arg Asn Thr Tyr Asp Asn Ala Ile Ser Thr Phe Lys Asp Val
130                 135                 140
Lys Val Glu Leu Ser Thr Ser Pro Asn Phe Glu Lys Asp Asn Thr Ser
145                 150                 155                 160
Val Val Phe Glu Lys Gln Asp Ile Ile Glu Ser Arg Glu Ser Lys Gly
            165                 170                 175
Asn Pro Gln Ile Ile Ser Leu Asp Lys Ala Ile Asp Ala Gln Tyr Ile
            180                 185                 190
Arg Ile Trp Gly Lys Gly His Tyr Ile Glu Asn Thr Asn Ser Ser Trp
            195                 200                 205
Lys Gly Tyr Ser Asn Gly Asn Leu Tyr Asn Glu Ile Glu Val Met Ala
            210                 215                 220
Asn Val Pro Lys Ser Glu Val Pro Ser Gln Pro Asp Asn Ile Gln Pro
225                 230                 235                 240
Arg Asn Leu Ala Ser Gly Lys Leu Pro Tyr Val Tyr Gly Leu Glu Pro
            245                 250                 255
Ser Asn Ile Glu Ala Ile Thr Asp Gly Lys Ile Asp Asp Asn Tyr Ala
            260                 265                 270
Val His Asn Ser Met Gly Asn Asn Trp Leu Gln Phe Glu Tyr Lys Asn
            275                 280                 285
Thr Tyr Lys Phe Asn Ser Ile Lys Phe Lys Leu Glu Pro Gly Asn Tyr
            290                 295                 300
Lys Ser Val Lys Val Ala Ile Ser Asn Ser Pro Asn Asn Gly Phe Lys
305                 310                 315                 320
Glu Val Phe Ser Lys Ile Asn Trp Thr Gln Asn Asn Asp Leu Glu Val
            325                 330                 335
Ile Asn Leu Pro Ser Asn Thr Lys Gly Arg Tyr Ile Arg Phe Thr Ile
            340                 345                 350
Asp Lys Asp Gly Lys Ser Lys Thr Lys Tyr Ser Glu Ile Glu Ile Trp
            355                 360                 365
Gly Thr Gly Asn Asn Tyr Asp Glu Ser Lys Asp Glu Tyr Val Glu Pro
            370                 375                 380
Gln Ser Lys Tyr Asn Glu Leu Val Trp Ser Asp Glu Phe Asn Gly Glu
385                 390                 395                 400
Lys Ile Asp Glu Asn Lys Trp Thr Ile Ile Asp Gly Met Val Asn His
            405                 410                 415
Gly Ala Ile Tyr Asn Arg Gly Ala Val Ser Ile Lys Lys Asp Gly Asn
            420                 425                 430
Asn Ser Tyr Leu Ala Ile Asn Thr Lys Asn Phe Asn Ser Thr Glu Glu
            435                 440                 445
Leu Ile Lys Ala Val Gly Val Asp Asn Tyr Leu Gly Gln Ser Ile Asn
450                 455                 460
Lys Gln Lys Val Thr Trp Ser Ser Gly Arg Ile Glu Ser Lys Asn Lys
465                 470                 475                 480
Tyr Ser Phe Gln Phe Gly Arg Met Ala Val Arg Ala Lys Val Asn Asp
            485                 490                 495
Ser Gln Gly Ile Trp Pro Ala Ile Trp Met Leu Ser Gln Asp Glu Thr
            500                 505                 510
```

```
Gly His Asp Glu Ile Asp Val Leu Glu Tyr Leu Gly Gln Asp Pro Trp
            515                 520                 525

Gly Ala Trp Thr Thr Asn His Phe Gly Ile Leu Gly Lys Asn Lys Ala
        530                 535                 540

Ser Asn Gly Ile Arg Asn Ser Asn Tyr Glu Ala Trp Ser Gln Asp Phe
545                 550                 555                 560

His Val Phe Glu Val Glu Trp Asp Pro Glu Phe Ile Lys Trp Tyr Ile
                565                 570                 575

Asp Gly Lys Glu Val Phe Gln Ser Thr Gln Gly Arg Asp Asp Gly Arg
            580                 585                 590

Asp Gly Met His Thr Arg Pro Met Phe Pro Ile Leu Glu Thr Gln Val
        595                 600                 605

Gly Asp Gly Trp Val Gly Asp Val Asp Tyr Asn Lys Gln Asn Thr Lys
610                 615                 620

Gln Asn Ser Asp Tyr Leu Ile Asp Trp Ile Arg Val Tyr Gln Met Pro
625                 630                 635                 640

Asn Gln Ala Asn Val Lys Phe Asp Asp Leu Arg Ser Leu Asp Lys Lys
            645                 650                 655

Glu Asn Lys Gly Tyr Glu Val Thr Pro Tyr Ser His Thr Asn Asn Leu
        660                 665                 670

Ile Lys Leu Ser Asp Gly Asp Leu Asn Glu Asn Lys Asp Asn Phe
675                 680                 685

Tyr Tyr Gly Gly Gln Pro Arg Leu Glu Asn Asn Arg Ile Ala Val Gly
            690                 695                 700

Glu Asn Gly Gly Arg Glu Ser Ile Ile Tyr Asn Val Thr Asn Val Lys
705                 710                 715                 720

Asp Ile His Leu Thr Thr Tyr Tyr Gln Thr Ile Glu Asp Lys Ile Thr
                725                 730                 735

Trp Asn Arg Ser Ala Gly Ala Tyr Glu Gly Tyr Ser Ile Arg Ser Ser
            740                 745                 750

Leu Ile Ser Gly Asn Ile Asp Phe Lys Leu Phe Thr Ser Asp Asp Gly
        755                 760                 765

Glu Ile Trp Asn Glu Val Arg Asn Val Lys Ile Val Asp Asn Phe Val
770                 775                 780

Glu Lys His Pro Gly Tyr Ala Arg Thr Thr Phe Asp Ala Tyr Asn Leu
785                 790                 795                 800

Pro Lys Asn Thr Gln Phe Ile Lys Ile Glu Phe Pro Gln Tyr Lys Asn
            805                 810                 815

Val Lys Tyr Arg Leu Asn Ser Gly Ala Ile Lys Asp Val Lys Asn Thr
        820                 825                 830

Asp Ile Gln Leu Ala Lys Val Thr Phe Leu Gln Asn Lys
            835                 840                 845

<210> SEQ ID NO 3
<211> LENGTH: 7
<212> TYPE: PRT
<213> ORGANISM: Clostridium perfringens

<400> SEQUENCE: 3

Ser Glu Val Pro Ser Gln Pro
 1               5

<210> SEQ ID NO 4
<211> LENGTH: 10
<212> TYPE: PRT
<213> ORGANISM: Clostridium perfringens
```

```
<400> SEQUENCE: 4

Leu Ser Asp Gly Asp Leu Asn Glu Glu Asn
 1               5                  10

<210> SEQ ID NO 5
<211> LENGTH: 10
<212> TYPE: PRT
<213> ORGANISM: Clostridium perfringens

<400> SEQUENCE: 5

Gln Asn Ser Asp Tyr Leu Ile Asp Trp Ile
 1               5                  10

<210> SEQ ID NO 6
<211> LENGTH: 21
<212> TYPE: PRT
<213> ORGANISM: Clostridium perfringens

<400> SEQUENCE: 6

Asp Glu Asn Glu Tyr Val Leu Thr Asn Val Leu Asn Gly Leu Ile Pro
 1               5                  10                  15

Thr Thr Asn Ser Lys
            20

<210> SEQ ID NO 7
<211> LENGTH: 17
<212> TYPE: DNA
<213> ORGANISM: Artificial Sequence
<220> FEATURE:
<223> OTHER INFORMATION: primer

<400> SEQUENCE: 7
gaygaraayg artaygt                                              17

<210> SEQ ID NO 8
<211> LENGTH: 20
<212> TYPE: DNA
<213> ORGANISM: Artificial Sequence
<220> FEATURE:
<223> OTHER INFORMATION: primer
<220> FEATURE:
<221> NAME/KEY: unsure
<222> LOCATION: (9)...(9)
<223> OTHER INFORMATION: n=g or t or c or a
<220> FEATURE:
<221> NAME/KEY: unsure
<222> LOCATION: (15)...(15)
<223> OTHER INFORMATION: n=g or t or c or a

<400> SEQUENCE: 8
tcytcrttna rrtcnccrtc                                           20

<210> SEQ ID NO 9
<211> LENGTH: 30
<212> TYPE: DNA
<213> ORGANISM: Artificial Sequence
<220> FEATURE:
<223> OTHER INFORMATION: primer

<400> SEQUENCE: 9
tgatacttgt ggtacagtag aatgcccact                                30

<210> SEQ ID NO 10
<211> LENGTH: 30
<212> TYPE: DNA
<213> ORGANISM: Artificial Sequence
```

```
<220> FEATURE:
<223> OTHER INFORMATION: primer

<400> SEQUENCE: 10
atgtttacta ttagtagtag gtattaagcc                                          30

<210> SEQ ID NO 11
<211> LENGTH: 30
<212> TYPE: DNA
<213> ORGANISM: Artificial Sequence
<220> FEATURE:
<223> OTHER INFORMATION: primer

<400> SEQUENCE: 11
agatggtatg catactagac ctatgttccc                                          30

<210> SEQ ID NO 12
<211> LENGTH: 30
<212> TYPE: DNA
<213> ORGANISM: Artificial Sequence
<220> FEATURE:
<223> OTHER INFORMATION: primer

<400> SEQUENCE: 12
aagttggaga tggttgggtt ggtgatgttg                                          30

<210> SEQ ID NO 13
<211> LENGTH: 42
<212> TYPE: DNA
<213> ORGANISM: Artificial Sequence
<220> FEATURE:
<223> OTHER INFORMATION: primer

<400> SEQUENCE: 13
gcagccgaat tcatgaaatt tttctcgaaa ttcaaaaagg ta                            42

<210> SEQ ID NO 14
<211> LENGTH: 42
<212> TYPE: DNA
<213> ORGANISM: Artificial Sequence
<220> FEATURE:
<223> OTHER INFORMATION: primer

<400> SEQUENCE: 14
gcgtcgctcg agttatttat tttgtaaaaa agttacttta gc                            42

<210> SEQ ID NO 15
<211> LENGTH: 20
<212> TYPE: DNA
<213> ORGANISM: Artificial Sequence
<220> FEATURE:
<223> OTHER INFORMATION: primer

<400> SEQUENCE: 15
ggtgcaatct ataataggggg                                                    20

<210> SEQ ID NO 16
<211> LENGTH: 20
<212> TYPE: DNA
<213> ORGANISM: Artificial Sequence
<220> FEATURE:
<223> OTHER INFORMATION: primer

<400> SEQUENCE: 16
cccctattat agattgcacc                                                     20
```

-continued

```
<210> SEQ ID NO 17
<211> LENGTH: 20
<212> TYPE: DNA
<213> ORGANISM: Artificial Sequence
<220> FEATURE:
<223> OTHER INFORMATION: primer

<400> SEQUENCE: 17
aagtctgaag taccaagtca                                              20

<210> SEQ ID NO 18
<211> LENGTH: 21
<212> TYPE: DNA
<213> ORGANISM: Artificial Sequence
<220> FEATURE:
<223> OTHER INFORMATION: primer

<400> SEQUENCE: 18
gaacttgttt ggagtgacga g                                            21

<210> SEQ ID NO 19
<211> LENGTH: 17
<212> TYPE: DNA
<213> ORGANISM: Artificial Sequence
<220> FEATURE:
<223> OTHER INFORMATION: primer

<400> SEQUENCE: 19
gtaaaacgac ggccagt                                                 17

<210> SEQ ID NO 20
<211> LENGTH: 19
<212> TYPE: DNA
<213> ORGANISM: Artificial Sequence
<220> FEATURE:
<223> OTHER INFORMATION: primer

<400> SEQUENCE: 20
ggaaacagct atgaccatg                                               19

<210> SEQ ID NO 21
<211> LENGTH: 20
<212> TYPE: DNA
<213> ORGANISM: Artificial Sequence
<220> FEATURE:
<223> OTHER INFORMATION: primer

<400> SEQUENCE: 21
tgacttggta cttcagactt                                              20
```

What is claimed is:

1. A method for producing a treated organ for transplantation showing suppressed rejection due to α-galactose antigens, which comprises treating an organ expressing α-galactose antigens with endo-β-galactosidase to produce the treated organ,
wherein the endo-β-galactosidase is a protein selected from the group consisting of (A) and (B):
   (A) a protein that comprises the amino acid sequence of SEQ ID NO: 2;
   (B) a protein that comprises the amino acid sequence of (A) including substitution deletion, or insertion of one to 40 amino acids and has endo-β-galactosidase activity.

2. The method according to claim 1, wherein the organ for transplantation is a swine organ.

3. The method according to claim 1, wherein the organ for transplantation is an organ for transplantation to a human.

4. The method according to claim 1, wherein the organ is kidney.

5. A method for treating an isolated organ, which comprises treating the isolated organ which expresses α-galactose antigens with endo-β-galactosidase,
wherein the endo-β-galactosidase is a protein selected from the group consisting of (A) and (B):
   (A) a protein that comprises the amino acid sequence of SEQ ID NO: 2;
   (B) a protein that comprises the amino acid sequence of (A) including substitution deletion, or insertion of one to 40 amino acids and has endo-β-galactosidase activity.

* * * * *

UNITED STATES PATENT AND TRADEMARK OFFICE
CERTIFICATE OF CORRECTION

PATENT NO. : 7,393,672 B2
APPLICATION NO. : 11/407596
DATED : July 1, 2008
INVENTOR(S) : Muramatsu et al.

It is certified that error appears in the above-identified patent and that said Letters Patent is hereby corrected as shown below:

Column 2, Line 32, "a cell is (hereinafter," should be changed to --a cell (hereinafter,--

Column 8, Line 26, "a pharmaceutical can, be" should be changed to --a pharmaceutical can be--

Column 9, Line 14, "unit/ml (6.04-0.05" should be changed to --unit/ml (0.04-0.05--

Column 10, Line 31, "2> PCR Using" should be changed to --<2> PCR Using--

Column 11, Line 23, "PGEM-T Easy Vector" should be changed to --pGEM-T Easy Vector--

Column 12, Line 47, "with 25 μm of FITC" should be changed to --with 25 μl of FITC--

Column 12, Line 52, "containing 0.2%. BSA," should be changed to --containing 0.2% BSA--

Column 13, Line 15, "containing 20 μl of" should be changed to --containing 20 μg of--

Column 14, Line 33, "electrosptay on source" should be changed to --electrospray on source--

Column 15, Line 57, "existence of complements"." should be changed to --existence of complement".--

Column 17, Line 9, "immunoglobulin inhuman plasma" should be changed to --immunoglobulin in human plasma--

Column 29, Lines 36-41,  "<222>   LOCATION: (9) . . . (9)
                         <223>   OTHER INFORMATION: n=g or t or c or a
                         <220>   FEATURE:
                         <221>   NAME/KEY: unsure
                         <222>   LOCATION (15) . . . (15)
                         <223>   OTHER INFORMATION: n=g or t or c or a"

UNITED STATES PATENT AND TRADEMARK OFFICE
CERTIFICATE OF CORRECTION

PATENT NO. : 7,393,672 B2
APPLICATION NO. : 11/407596
DATED : July 1, 2008
INVENTOR(S) : Muramatsu et al.

It is certified that error appears in the above-identified patent and that said Letters Patent is hereby corrected as shown below:

should be changed to

--<222>    LOCATION: (9) . . . (5)
      <223>    OTHER INFORMATION: n=a or g or c or t--

Column 33, Line 64, "substitution deletion," should be changed to --substitution, deletion--

Column 34, Line 64 "substitution deletion," should be changed to --substitution, deletion--

Signed and Sealed this

Twenty-third Day of December, 2008

JON W. DUDAS
*Director of the United States Patent and Trademark Office*